United States Patent [19]

Carlsson et al.

[11] 4,102,887
[45] Jul. 25, 1978

[54] INTERMEDIATES USED IN THE PREPARATION OF PHENYL-PYRIDYLAMINE DERIVATIVES

[76] Inventors: Per Arvid Emil Carlsson, Torild Wulffsgatan 50, S-143 19 Göteborg; Bernt Sigfrid Emanuel Carnmalm, Tornrosavagen 14; Svante Bertil Ross, Hedvagen 8, both of, S-151 52 Södertalje; Carl Bengt Johan Ulff, Agardevagen 9, S-151 47 Sodertalje, all of Sweden

[21] Appl. No.: 762,056

[22] Filed: Jan. 24, 1977

Related U.S. Application Data

[63] Continuation-in-part of Ser. No. 632,698, Nov. 17, 1975, abandoned.

[30] Foreign Application Priority Data

Nov. 21, 1974 [SE] Sweden ............................. 7414622

[51] Int. Cl.² .................. C07D 213/26; C07D 213/52
[52] U.S. Cl. ...................... 260/290 HL; 260/294.8 R; 260/294.8 F; 260/297 R
[58] Field of Search ..... 260/290 HL, 297 R, 294.8 R, 260/294.8 F

[56] References Cited

U.S. PATENT DOCUMENTS 2,898,338  8/1959  Villani ........................... 260/290 HL

*Primary Examiner*—Alan L. Rotman

*Attorney, Agent, or Firm*—Brumbaugh, Graves, Donohue & Raymond

[57] ABSTRACT

A compound having the formula

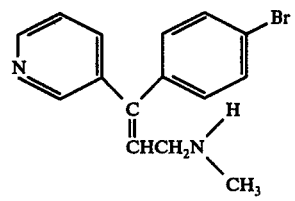

processes for preparing such a compound, intermediates such as

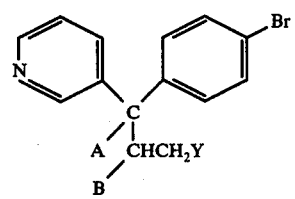

used in the preparation thereof where A and B together form a second bond or A is OH and B is H and where Y is a splittable group, and pharmaceutical compositions and a method for the treatment of depression and relief of anxiety.

5 Claims, No Drawings

INTERMEDIATES USED IN THE PREPARATION OF PHENYL-PYRIDYLAMINE DERIVATIVES

This application is a continuation in part of Ser. No. 632,698 filed Nov. 17, 1975 and claims the benefit of the priority of parent application, Serial No. 632,698 filed Nov. 17, 1975 now abandoned.

The present invention is related to new compounds having therapeutic activity and to methods for their preparation. The invention is also related to the preparation of pharmaceutical compositions containing at least one of the compounds and to methods for their pharmacological use.

PRIOR ART

Depressive disorders have with more or less success been treated with various compounds.

The antidepressive agents which have received the most widespread, clinical use are the tricyclic tertiary amines imipramine having the structure formula

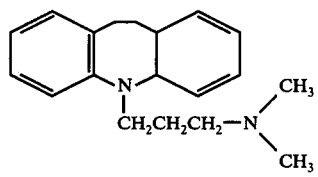

and amitripytyline having the structure formula

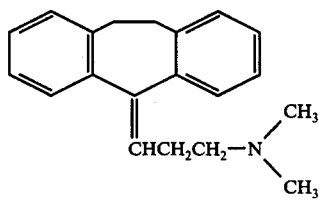

Secondary amines such as desipriamine having the structure formula

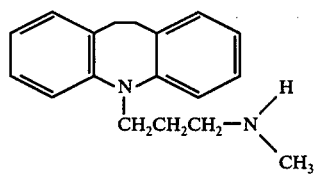

and nortriptyline having the structure formula

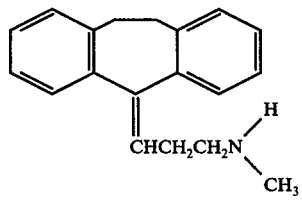

are used to a somewhat less extent. These substances have, however, side effects that are not desired in therapeutic use, such as orthostatism, anticholinergic effects and above all, an arrhythmogenic i.e. heart arrhythmia developing effect when administered in large doses to old patients. Moreover, all the substances mentioned show the drawback that the antidepressive effect does not start until some weeks after treatment. Further, it is known from the literature that certain 1,1-diphenyl-3-aminoprop-1-enes, such as the compound having the formula

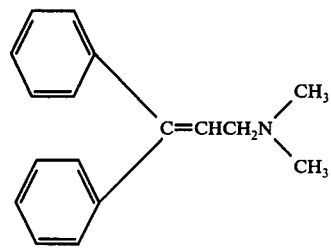

have an antidepressive effect, of J. Med. Chem. 14, 161-4 (1971). Compounds having the formula

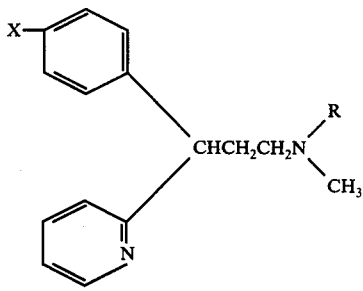

wherein X is chlorine or bromine and R is hydrogen or methyl, are described as having antidepressive effect, of U.S. Pat. No. 3,423,510, these compounds however also have a strong antihistaminic effect. From the literature it is also known that a compound having the formula

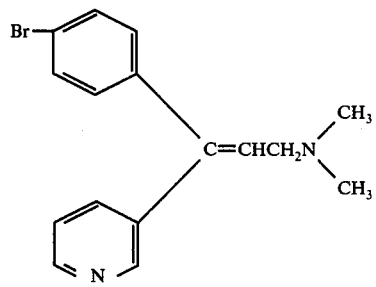

has an antidepressive activity in animal models, cf. Belgian Pat. Specification No. 781,105.

In clinical practice different types of depressive disorders are recognized. Depressed patients respond in different ways to the various anti-depressants. Most of these substances inhibit the neuronal uptake of noradrenaline, and some of them additionally inhibit the uptake of 5-hydroxytryptamine. It is believed that inhibition of the uptake of 5-hydroxytryptamine is the mechanism behind a mood elevating property seen in some of these anti-depressants. In addition to the absolute values for inhibition of the uptake of either 5-hydroxytryptamine or noradrenaline the selectivity towards uptake of either of these two amines is of great interest.

OUTLINE OF THE INVENTION

(a) GENERAL OUTLINE

A main object of the present invention is to obtain a new compound having a good antidepressive effect. A further object of the invention is to obtain a compound having an antidepressive effect, and giving rise to only minor side-effects, in particular arrhythmogenic effects. Another object is to obtain compounds having a therapeutic effect against anxiety. Further objects of the invention will be evident from the following description.

The compound of the invention is characterized by the formula

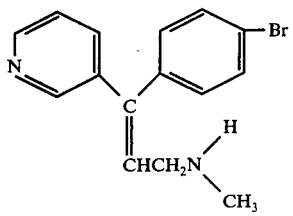

I

Pharmaceutically acceptable salts of this compound are included within this invention.

Due to the lack of free rotation in the double bond the compound of this invention may exist in different stereoisomeric forms, that is in cis-trans isomers or, according to the IUPAC nomenclature (J. Org. Chem. 35, 2849–2867, September 1970), in an E-form and a Z-form. The compound may be used therapeutically as a mixture of geometrical isomers or in pure E or Z form. The pure geometrical isomers may be prepared from an isomer mixture, from an isomer-pure starting material or directly by a stereoselective synthesis.

The compound of this invention may be administered in the form of a free base or a salt thereof with non-toxic acids. Some typical examples of these salts are the hydrobromide, hydrochloride, phosphate, sulphate, sulphamate, lactate, acetate, citrate, tartrate, malate and maleate.

(b) PHARMACEUTICAL COMPOSITIONS

In clinical practice the compounds of the present invention will normally be administered orally, rectally or by injection, in the form of pharmaceutical compositions comprising the active ingredient either as a free base or as a pharmaceutically acceptable, non-toxic acid addition salt, e.g. as one of those suggested above in association with a pharmaceutically acceptable carrier. Accordingly, terms relating to the novel compound of this invention are intended to include both the free amine base and the acid addition salts of the free base, unless the context in which such terms are used, e.g. in the specific examples would be inconsistent with the broad concept. The carrier may be a solid, semisolid or liquid diluent, or a capsule. These pharmaceutical compositions constitute a further aspect of this invention. Usually the active substance will constitute from 0.1 to 95% by weight of the composition, more specifically from 0.5 to 20% by weight for compositions intended for injection and from 2 to 50% by weight for compositions suitable for oral administration.

To produce pharmaceutical compositions containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calcium stearate or polyethylene glycol waxes, and then compressed to form tablets. If coated tablets are required, the cores, prepared as described above, may be coated with a concentrated sugar solution which may contain, e.g. gum arabic, gelatine, talcum or titanium dioxide. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine and, for example, glycerol, or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally such liquid preparations may contain coloring agents, flavoring agents, saccharine and carboxymethylcellulose as a thickening agent.

Solutions for parenteral applications by injection can be prepared in an aqueous solution of water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutic treatment is 25 to 250 mg for peroral administration, preferably 50 to 150 mg and 5 to 50 mg for parenteral administration, preferably 10 to 30 mg. A preparation in dosage unit form for oral administration may contain 10–50 mg, preferably 10 to 25 mg of active substance per dosage unit.

(c) PREFERRED EMBODIMENT

The preferred isomer of the compound of the invention is the Z-isomer having the structural formula

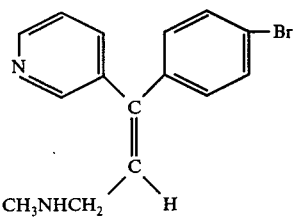

Preferably the compound of the invention will be prepared and used in the form of its salt.

(d) METHODS OF PREPARATION

Method A, Dehydration of a compound of the formula

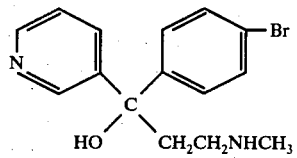

to a compound of the formula I.

The dehydration of the starting material may for example be done by means of treatment with sulpuric acid and heating of the reacting mixture. The dehydration of the starting material may also be done by means of other types of acid-catalysis, such as by means of hydrochloric acid, HCl, phosphoric acid, $H_3PO_4$, potassium hydrogen sulphate, $KHSO_4$, or oxalic acid $(COOH)_2$. Other methods for the dehydration of the starting material to form a compound of the formula I are dehydration using phosphoroxichloride $POCl_3$ in pyridine, and dehydration with thionylchloride, $SOCl_2$, in pyridine. Also catalytic dehydration of the starting material may be used. The dehydration is in this case carried out at a temperature of about 300° to 500° C using a catalyst such as kaolin, alumina or aluminum oxide. Method B. Demethylation of a compound of the formula

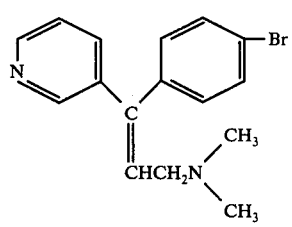

to form a compound of the formula I.

Method C. Alkylation of monomethylamine with a compound of the formula

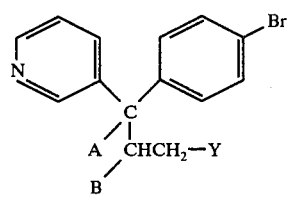

wherein A and B together form a second bond or A is OH and B is H, and wherein Y is a splittable group to form a compound of the formula I. When A is OH and B is H, the alkylation step can take place either simultaneously with or subsequent to a dehydration step.

Illustrative examples of Y are halogens such as Cl, Br and I or sulphonates such as methanesulphonate, toluenesulphonate and benzene-sulphonate.

Method D. Introduction of a methyl group into a compound of the formula

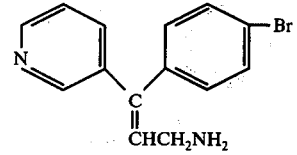

to a compound of the formula I.

Method E. Treatment under hydrolytic conditions of an acyl or sulphonyl compound of the formula

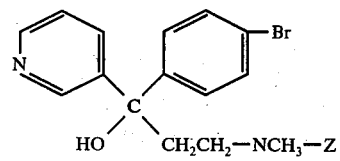

wherein Z is an acyl or sulphonyl group to form a compound of the formula I either directly or via an intermediate of the formula

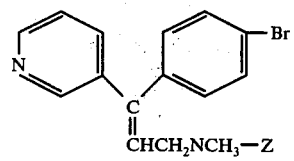

Illustrative examples of Z are acetyl, benzoyl, methanesulphonyl, benzoylmethanesulphonyl and toluenesulphonyl.

(e) INTERMEDIATES

For the preparation of the compounds of formula I it has been found that certain hitherto unknown compounds may be valuable.

When preparing the compounds of formula I according to process A, the compound

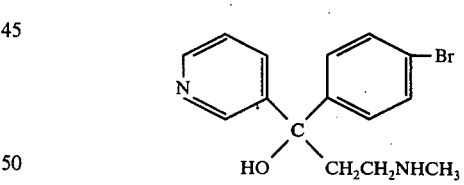

is used as starting material.

This starting material can be prepared according to the reaction scheme

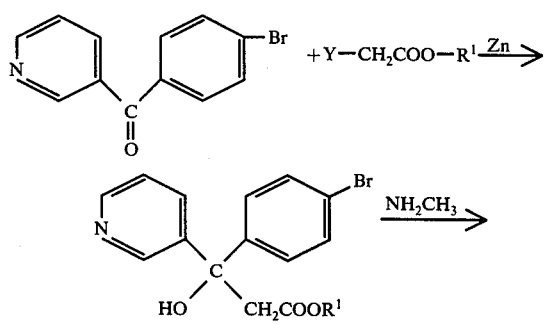

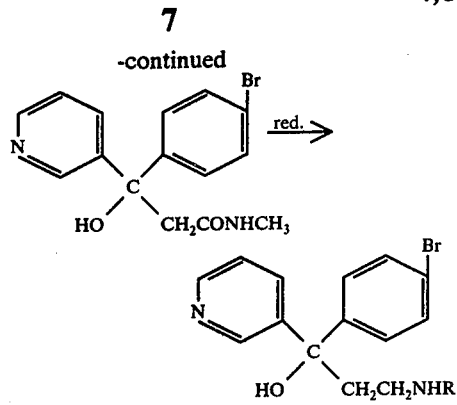

In the reaction scheme Y has the previously given definition and $R^1$ is a lower alkyl group with 1–5 carbon atoms, preferably an ethyl group. The reduction in the last step is preferably carried out with a hydride reagent.

When preparing the compound of the formula I according to process C, compounds of the formula

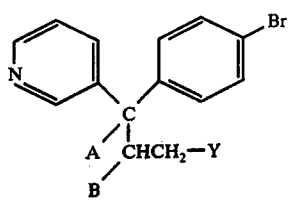

wherein A and B together form a second bond or A is OH and B is H, and wherein Y is a splitable group are used as starting material. Suitable Y groups include halogen, such as Cl, Br and I, or sulfonates, such as methanesulfonate, toluenesulfonate and benzene-sulfonate.

This starting material can be prepared according to the reaction scheme

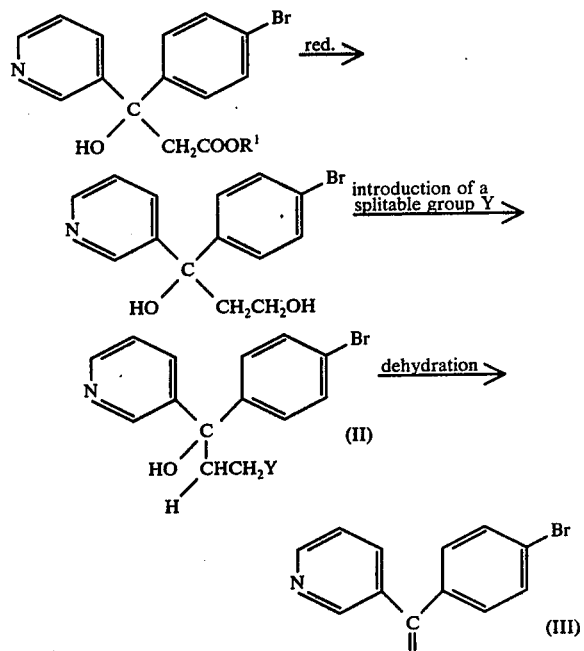

In the reaction scheme above A, B, Y and $R^1$ have the previously given definitions. The reduction in the first step is preferably carried out using $LiAlH_4$. The introduction of the splitable group Y is preferably accomplished using a phosphorous halogenide such as $PBr_3$ or $PCl_3$ which gives a compound of formula III wherein Y is halogen such as Br or Cl or a sulphonyl halogenide such as toluenesulfonylchloride or methanesulfonylchloride preferably in the presence of a base such as pyridine, which gives a compound of formula III wherein Y is a sulfonate such as toluenesulfonate or methanesulfonate. Also, the steps of introducing the Y group and dehydrating can take place simultaneously.

The same starting material in which the splitable group is a halogen may also be obtained by the following reaction scheme:

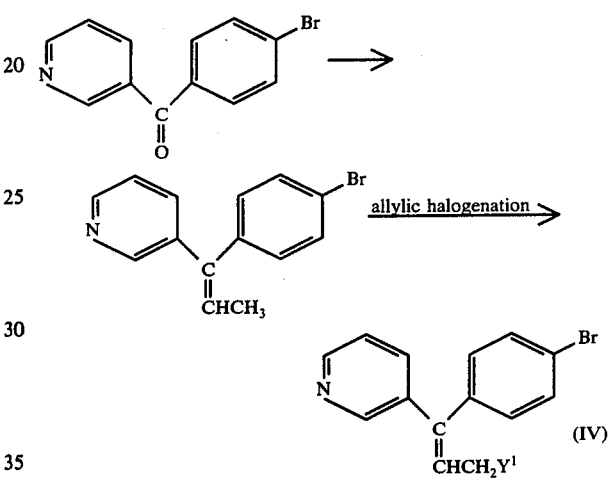

wherein $Y^1$ is a halogen such as Cl, Br or I. Suitable reactants for the first step include sodium hydride and triphenylethyl phosphonium halides. Other reactants which may be useful for carrying out the first step are those having a nucleophilic ethyl group e.g. a Grignard reagent such as $C_2H_5MgBr$. The reaction with such reagents should be followed by abstraction of water. The allylic halogenation is carried out with a suitable halogenating agent such as a halogen succinimide.

The intermediate compounds of formula II and III above are very useful in the preparation of the 3-(4-bromophenyl)-N-methyl-3-(4-pyridyl)-allylamines of the present invention and also of the 3-(4-bromophenyl)-N,N-dimethyl-3-(3-pyridyl) allylamines disclosed in U.S. Pat. Nos. 3,928,613 and 3,928,369.

When preparing the compound of the invention according to process D a compound of the formula

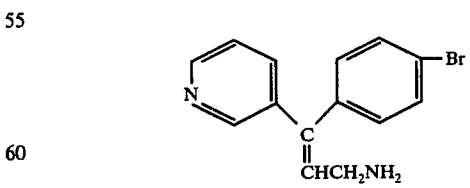

is used as starting material. This compound may be prepared according to methods similar to methods A, B, C and E described in paragraph d).

Still further methods exist for the preparation of the starting material, for instance according to the reaction scheme:

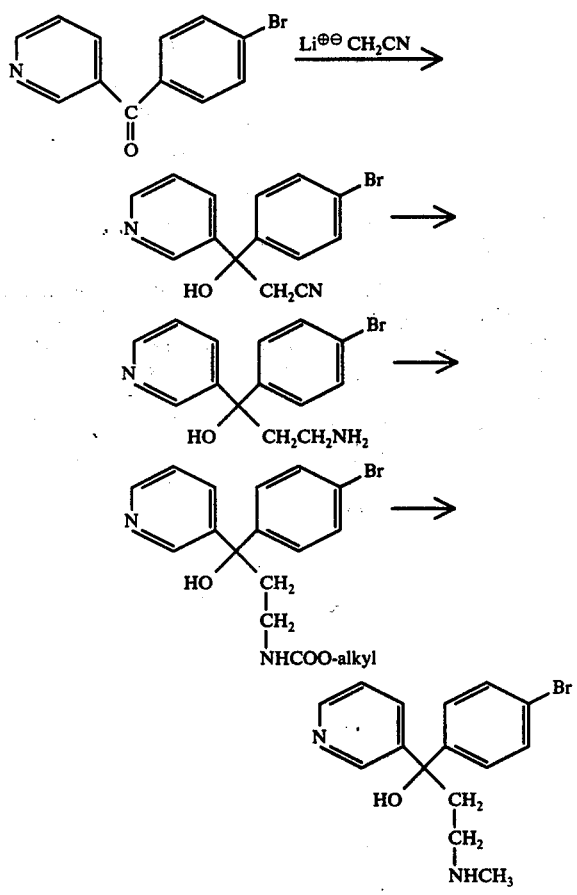

(f) WORKING EXAMPLES

Preparation of intermediates

Example A

Step 1

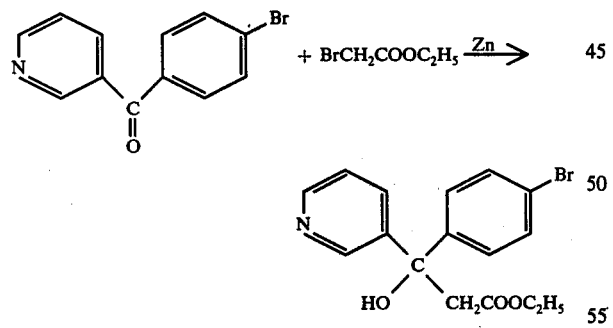

A mixture of 4-bromophenyl-3-pyridylketone [CA 66, 37125$^h$ (1967); 50 g, 0.19 moles] and activated zinc (20 g) in benzene (100 ml) was heated to reflux. Ethyl bromoacetate (56 g, 0.35 moles) dissolved in benzene (50 ml) was added carefully during 30 minutes. Another portion of zinc (50 g) was added and the mixture was refluxed for 14 hours. After cooling and filtration, benzene (300 ml) was added to the filtrate, which was washed three times with 10% aqueous acetic acid solution.

Ethyl ether (200 ml) was added and the solution acidified with 10% hydrochloric acid. The precipitate was filtered off, washed with ether and dried. Yield: 75%. M.p. 168°–175° C.

Step 2

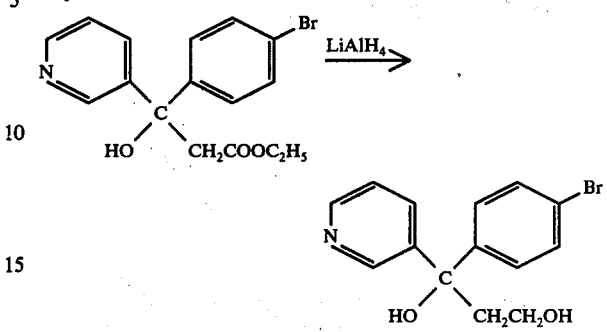

The base (9.5 g, 0.027 moles) from ethyl 3-(4-bromophenyl)-3-hydroxy-3-(3-pyridyl)propanoate hydrochloride (step 1) was prepared and dissolved in ethyl ether (50 ml). This solution was added dropwise to an ice-cold mixture of lithium aluminium hydride (1.0 g, 0.027 moles) and ethyl ether (150 ml). The reaction mixture was refluxed for 5 hours, cooled and a saturated sodium sulphate solution was added until a white precipitate was formed. This was filtered off and the filtrate evaporated. The residue was crystallized from chloroform. 1-(4-bromophenyl)-1-(3-pyridyl)-1,3-propanediol was obtained. Yield: 39%. M.p. 130°–132° C.

EXAMPLE B

Step 1

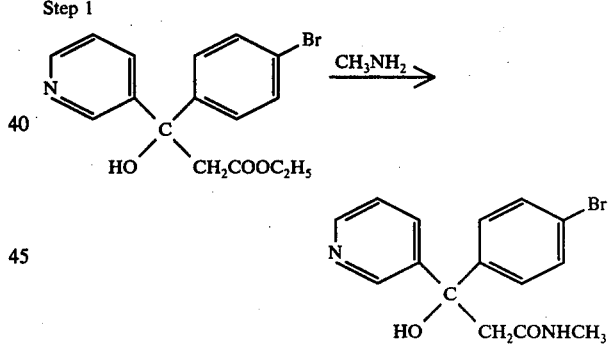

3-(4-bromophenyl)-3-hydroxy-N-methyl-3-(3-pyridyl)-propionamide 19.4 g (0.05 mole) of ethyl 3-(4-bromophenyl)-3-hydroxy-3-(3-pyridyl)-propanoate, 200 ml of 40% solution of methylamine in water and 30 ml of absolute ethanol was stirred for 24 hours at room temperature. The precipitate was filtered off and recrystallized from isopropyl alcohol, which gave 13.2 g (79%) of the amide. M.p. 188°–191° C. The formula $C_{15}H_{15}BrN_2O_2$ was verified through elemental analysis. (The elemental analyses throughout this application were carried out for all elements of the compounds prepared, and are within ± 0.4 percent of the theoretical values if not otherwise stated.)

Step 2

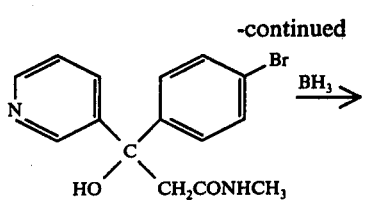

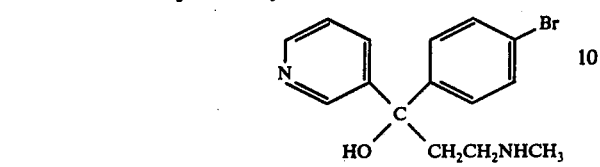

3-(4-bromophenyl)-3-hydroxy-N-methyl-3-(pyridyl)-propylamine

To 1.0 g (3.1 mmole) of 3-(4-bromophenyl)-3-hydroxy-N-methyl-3-(3-pyridyl)-propionamide and 0.8 g (0.02 mole) of sodium borohydride in 60 ml of dry tetrahydrofuran at 0° and under $N_2$, was added dropwise over 20 minutes 4.6 (0.03 mole) of boron trifluoride ethyl etherate in 20 ml of dry tetrahydrofuran. The mixture was stirred over night at room temperature, and then cautiously hydrolyzed with water. Alcalization with 2M NaOH and extraction with ether gave after evaporation 0.9 of a semicrystalline residue. Recrystallization from etherpetroleum ether gave 0.2 g (23%) of the amine. M.p. 81°-88° C.

EXAMPLE C

Step 1

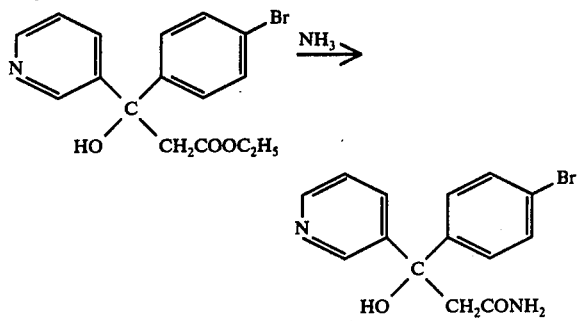

3-(4-bromophenyl)-3-hydroxy-3-(3-pyridyl)-propionamide 0.8 g (2.5 mmole) of ethyl 3-(4-bromophenyl)-3-hydroxy-3-(3-pyridyl)-propanoate, 50 ml of aqueous ammonia and 10 ml of absolute ethanol was stirred at room temperature for 24 hours. The white precipitate obtained was collected by filtration. Recrystallization from isopropyl alcohol gave 0.45 g (56%), m.p. 213°-214° C. The formula $C_{14}H_{13}BrN_2O_2$ was verified through elemental analysis, C calculated 52.4, found 51.9.

Step 2

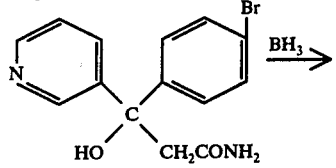

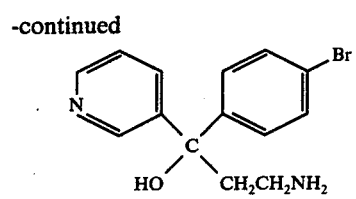

3-(4-bromophenyl)-3-hydroxy-3-(3-pyridyl)-propylamine

To 1.0 g (3.1 mmole) of 3-(4-bromophenyl)-3-hydroxy-3-(3-pyridyl)-propionamide and 0.8 g (0.02 mole) of sodium borohydride in 60 ml of dry tetrahydrofuran at 0° C and under $N_2$, was added dropwise over 20 minutes 4.6 g (0.03 mole) of boron trifluoride ethyl etherate in 20 ml of dry tetrahydrofuran. The mixture was stirred for 48 hours at room temperature, and then cautiously hydrolyzed with water. Alcalization with 2M NaOH and extraction with ether gave after evaporation a semi-crystalline residue. Recrystallization from ether-petroleum ether gave 0.6 g (63%) of the amine, m.p. 95°-115° C NMR-spectrum ($COCl_3$): $2H(2.4, 1-CH_2)_m$: $2H(3.0, 2-CH_2)_m$: $3H(3.6, —OH, —NH_2)_b$: $6H(7.1-8.0$ ArH$)_m$: $2H(8.6)_m$ Step 3

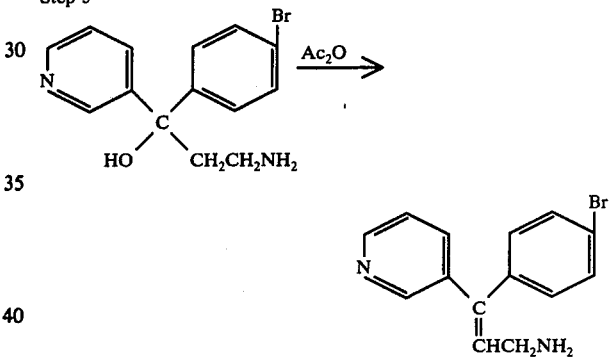

3-(4-bromophenyl)-3-(3-pyridyl)-allylamine

The raw product of 3-(4-bromophenyl)-3-hydroxy3(3-pyridyl)-propylamine (from 0.4 g of 3-(4-bromophenyl)-3-hydroxy-3-pyridyl)-propionamide was added with stirring to 50 ml of acetic anhydride and 0.25 ml of concentrated sulphuric acid and the mixture was heated at 130° for 45 minutes. The mixture was then cooled, poured onto crushed ice, alcalized with 30% NaOH and extracted with ether. Evaporation gave 0.36 g of an oil. After hydrolysis with 15 ml of concentrated hydrochloric acid for four hours 0.25 g of an oil was obtained. Thin layer cromatography showed two spots with $R_f$=0.1 and 0.8. Column chromatography on Silica Gel with methanol as eluant gave 0.06 g of the faster moving fraction and 0.19 g of the slower one, which was the amine. The oxalate of this compound was prepared. It was recrystallized from ethanol, M.p. 153.5°-155.5° C.

The NMR spectrum shows the vinyl proton as a double triplet at 6.1-6.5 ppm indicating an isomer ratio of 1:1. The formula: $C_{14}H_{13}BrN_2 \cdot 1$ $H_2O$ was verified through elemental analysis.

The oxalate was further recrystallized from a mixture of equal volumes of methanol and isopropyl alcohol and once from pure methanol. A substance melting at 160°–162° C was obtained. The NMR spectrum showed it to be the Z isomer.

EXAMPLE D

Step 1

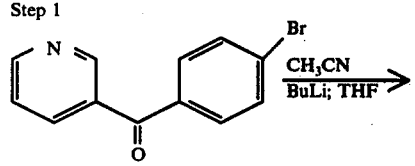

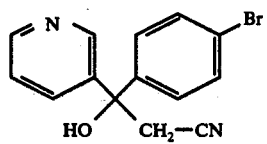

3-(4-bromophenyl)-3-hydroxy-3-(3-pyridyl)-propionitrile

A mixture of 6.5 g (0.16 mole) of acetonitrile and 50 ml of dry tetrahydrofuran (THF) was slowly added under $N_2$-atm to a mixture of 100 ml of 1.5 M n-butyllithium in hexane and 50 ml of dry THF at −50° C. After stirring for 35 minutes a solution of 36.5 g (0.14 mole) of 4-bromophenyl-3-pyridylketone in 250 ml of dry THF was added at −50° C. The temperature was kept at −70° C for 15 minutes, then the reaction mixture became viscous and it was allowed to reach ambient temperature. The product was poured into a stirred mixture of 500 g of icewater and 500 ml of methylene chloride. The layers were separated and the aqueous layer was extracted with 2×200 ml of $CH_2Cl_2$. The combined organic layers were washed with water and dried. The solvent was evaporated giving 39.7 g of an oil. It was dissolved in 550 ml of hot i-PrOH and a solution of 35 ml of 4M HCl-ether (0.14 mole) in 100 ml of i-PrOH was added. After cooling there was collected 34.6 g (74%) of the hydrochloride of 3-(4-bromophenyl)-3-hydroxy-3-(3-pyridyl)-propionitrile. M.p. 158°–161° C.

Step 2

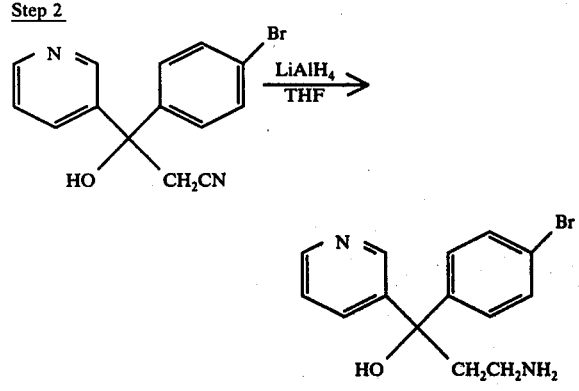

3-(4-bromophenyl-3-hydroxy-3-(3-pyridyl)-propylamine 17.2 g (0.056 mole) of 3-(4-bromophenyl)-3-hydroxy-3-(3-pyridyl)-propionitrile was dissolved in 175 ml of THF and diluted with 200 ml of ether. The solution was cooled to −35° C and 4.0 g (0.112 mole) of $LiAlH_4$ was added in portions under $N_2$−atm. The mixture was held at 0° C for 2 hours then at 15° C for 2 hours. 20ml of a solution of saturated $Na_2SO_4$ was slowly added. After 30 minutes the mixture was filtered and the inorganic salts were washed with 2×100 ml of ether. The filtrate was collected and the solvent was evaporated giving 14.7 g of an oil. It was diluted with 500 ml of hog i-PrOH and 4.3 g (0.048 mole) of oxalic acid in 300 ml of hot i-PrOH was dropwise added. After cooling over night 11.8 g of crystals, m.p. 98°–105° C were collected. An analytical sample of the free amine had m.p. 118°–120° C from i-PrOH. Yield 51%.

Step 3

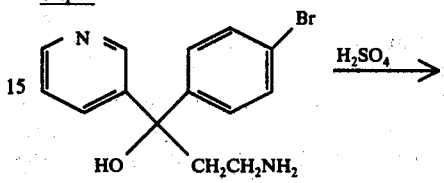

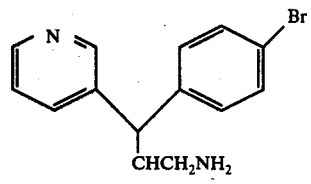

3-(4-bromophenyl)-3-(3-pyridyl)-allylamine

To 0.80 g (0.002 mole) of the oxalate of 3-(4-bromophenyl)-3-hydroxy-3-(3-pyridyl)-propylamine was added 6 ml of 70% $H_2SO_4$ for 35 minutes. Ice-water was added, then 30 ml of 30% NaOH and the mixture was extracted with 3×100 ml of ether. Drying and evaporation of the solvent gave 0.62 g of an oil. This was dissolved in 10 ml of hot ethanol and a hot solution of 0.20 g of oxalic acid in 5 ml of ethanol was added. Upon cooling, 0.49 g of crystals were collected. NMR showed the product to be a mixture of E and Z isomers of 3-(4-bromophenyl)-3-(3-pyridyl)-allylamine as in Example C step 3.

EXAMPLE E

Step 1

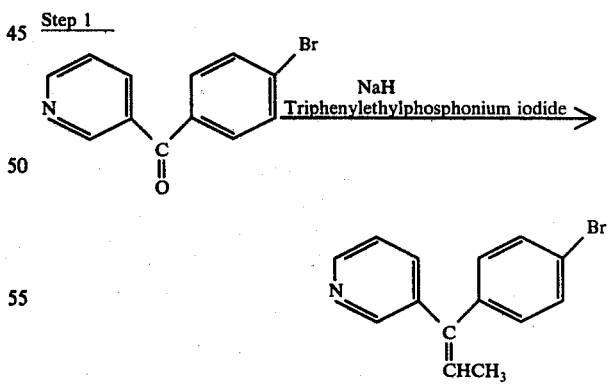

1-(4-bromophenyl)-1-(3-pyridyl)propene

A mixture of sodium hydride (3.0 g) and dimethylsulfoxide (DMSO) (100 ml) was heated at 85° C for 30 min. Triphenylethylphosphonium iodide (25 g) in DMSO (100 ml) was then added at ambient temperature, and after 30 minutes 4-bromophenyl-3-pyridyl ketone (11.2 g) in tetrahydrofurane was added. After one addtional hour the mixture was poured into icewater (1.5 l.). Extraction with ether, washing, drying and evaportion of the ether phase gave a partly crystalline residue, which was mixed with diethyl ether (100 ml) and diisopropyl ether (100 ml) and set aside in the cold. After 1 hour −5° C, the solid material (Ph₃PO) was filtered off and the filtrate distilled. The product 1-(4-bromophenyl)-1-(3-pyridyl) propene, boiled at 110°-120° C/1.5 Pa, $n_D^{25}$ 1.627. The yield was 10.8 g (90%). Thin layer chromatography (TLC) on silia in a mixture of methanol-diisopropylether (1+20) showed two spots with $R_f$ values of 0.32 and 0.29, respectively. Column chromatography of 1.4 g of the product on 90 g Si-gel (0.063–0.200 mm) in diisopropylether gave (after elution with 5% methanol in diisopropylether) 0.4 g of the pure α-isomer. The oxalate was prepared and recrystallized from 15 ml of methylisobutylketone. Mp. 120°-121° C. Analysis: Calculated %C 52.77, found 52.10; calculated %H 3.87, found 3.85; calculated %Br 21.94, found 22.80; calculated %N 3.85, found 3.70; and calculated %O 17.57, found 17.60.

Step 2

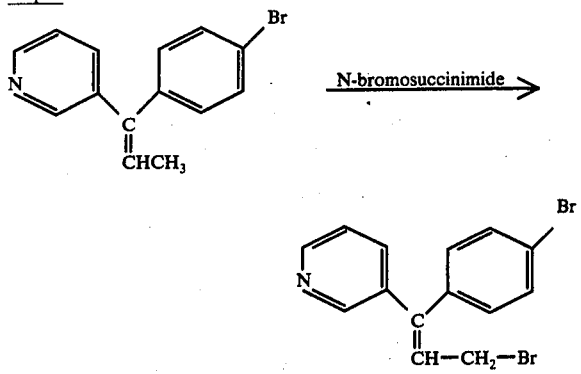

3-(4-bromophenyl)-3-(3-pyridyl)allylbromide

A mixture of 7.0 g (0.024 mol) of 1-(4-bromophenyl)-1-(3-pyridyl)-propene and 4.6 g (0.024 mol) of N-bromosuccinimide in 600 ml of carbontetrachloride was heated with stirring to 80° C. Then 0.5 g. of α,α-azabisbutylnitrile was added as radical initiator and the mixture was refluxed for 2 hours. After cooling to ambient temperature, the reaction mixture was filtered and the filtrate was evaporated in vacuo to 100 ml. NMR on the residual solution indicated a 1:1-mixture of the E- and Z-3-(4-bromophenyl)-3-(3-pyridyl)allylbromides. This solution was used directly in the preparation of the end product without further purification.

EXAMPLE F

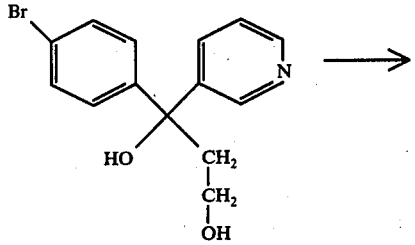

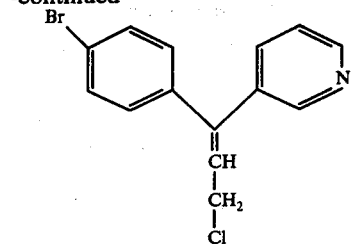

5 g of 1-(4-bromophenyl)-1-(3-pyridyl)-1,3-propanediol was converted into its hydrochloride by treatment with gaseous HCl in acetone. After evaporation of the acetone the residue was mixed with 25 ml of CH₂Cl₂ and then 4.5 g (3 ml) of PCl₃ was added dropwise with stirring and cooling. When all PCl₃ had been added the mixture was heated under reflux for 2 hours. A precipitate, which formed, was filtered off and found to give spectra not consistent with the structure of the desired product. The filtrate was heated over night, cooled and poured on ice. The mixture was neutralized with Na₂CO₃, the organic layer washed with water, dried and the solvent was evaporated. 2 g of an oil was obtained. Thin layer chromatography (Merck Fertigplatten, acetone) of this oil showed a product with a $R_f$-value of 0.67 together with a small amount of starting material ($R_f$=0.53). NMR spectroscopy showed the oil to be mainly the desired product 3-(4-bromophenyl)-3-(3-pyridyl) allyl chloride. From an ether solution of this oil the solid hydrochloride was precipitated by ethereal hydrogen chloride.

PREPARATION OF THE END PRODUCT

EXAMPLE 1, (METHOD C)

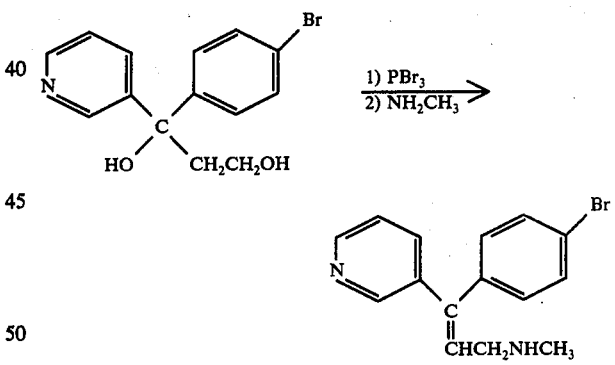

1-(4-bromophenyl)-1-(3-pyridyl)-1,3-propanediol (prepared in accordance with Example A, 7.2 g, 0.023 moles) was dissolved in dry acetone (70 ml). Hydrogen bromide was bubbled through the solution and the solvent was removed in vacuum. Methylene chloride (50 ml) and phosphorus tribromide (6.4 g, 0.047 mole) were added to the residue and the mixture was refluxed for 14 hours, poured into ice and made alkaline with sodium carbonate. Methanol (50 ml) was added to the organic phase and the solution was heated with monomethylamine (14 g, 0.47 mole) in an autoclave at 110° C for 15 hours. After cooling, the solvent was evaporated and the residue was dissolved in ether (25 ml) and water (25 ml). The pH of the mixture was adjusted to 9.0 with ammonia and the layers were separated. Another portion of water was added to the ethereal layer and pH was adjusted to 2.1 with HCl. The water-phase was treated with carbon black and then made alkaline with ammonia and extracted with ether. The organic-phase was dried with sodium sulphate and evaporated in vacuum. The residual base was dissolved in ether (40 ml) and cooled on an ice bath. Hydrochloric acid in ether was added dropwise whereupon a slightly yellow precipitate was obtained. The precipitate was filtered off, washed with ether and dried in vacuum. The hydrochloride of 3-(4-bromophenyl)-N-methyl-3-(3-pyridyl)-allylamine was obtained. Yield: 43% M.P. 138°-144° C.

EXAMPLE 2 (Method C)

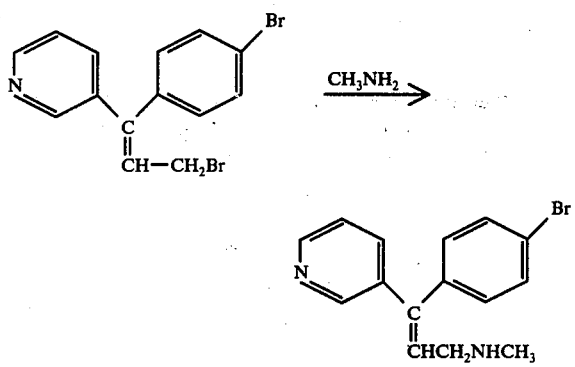

N-methyl-3-(4-bromophenyl)-3-(3-pyridyl)allylamine oxalate

To a carbontetrachloride solution of 0.003 mol crude 1-(4-bromophenyl)-1-(3-pyridyl)allyl bromide prepared as in Exampl E above, 3 ml of an aqueous solution (40%) of methylamine (0.040 mol) was added with stirring at room temperature. Stirring was continued for 60 hours then the solvent was evaporated in vacuo. The residue was mixed with diluted sodium hydroxide and extracted with diethylether. The combined organic layers were shaken with 3 × 100 ml 1 M HCl. The aqueous layers were combined and made alkaline by addition of 30% NaOH. Extraction with methylene chloride, drying and evaporation of the solvent gave 1.2 g of an oil. TLC on silica in diisopropylether - methanol - triethylamine (30:20:1) showed a spot at $R_f=0.07$, identical with that of an authentic sample of N-methyl-3-(4-bromophenyl)-3-(3-pyridyl)-allylamine, along with additional spots of higher $R_f$-values. Separation on 120 g Si-gel (0.063 - 0.200 mm) in diisopropylether - methanol (1:1) gave 0.4 g of the pure amine as a mixture of the E- and Z-forms, according to the double triplet at 6.3 ppm in the NMR spectrum. The amine was diluted with 15 ml isopropylalcohol and added to a hot solution of 0.15 g oxalic acid dihydrate in 15 ml of methanol. The crystals of the oxalate were filtered and air dried. Yield 0.34 g (26%), mp. 162°-165° C.

EXAMPLE 3 (METHOD C)

A mixture of 6.9 g of (Z)-3-(4-bromophenyl)-3-(3-pyridyl) allyl chloride (m.p. 188°-192° C, from actone; $R_f \sim 0.85$, silica acetone); 24 ml of methylamine (anhydrous) and 600 ml of ethanol were stirred at room temperature for about 48 hours. The solvent was evaporated, and (Z)-3-(4-bromophenyl)-3-(3-pyridyl)-N-methyl-allylamine was extracted and purified as the oxalate, which crystallized from 2-propanol giving 8.9 g melting at 206°-209° C. From this oxalate the amine hydrochloride was prepared. M.p. 162°-7° C from acetonitrile containing ~5% water.

EXAMPLE 4. (METHOD C)

7 g of (E)-3-(4-bromophenyl)-3-(3-pyridyl) allyl chloride (m.p. 170°-174° C, $R_f \sim 0.8$ silica acetone), 25 ml of methylamine and 600 ml of ethanol were mixed and stirred for about 24 hours. The oxalate of (E)-3-(4-bromophenyl)-3-(3-pyridyl)-N-methyl-allylamine was prepared as for the (Z) isomer and recrystallized from acetonitrile containing 15% water. 6 g melting at 214°-217° C was secured.

EXAMPLE 5 (METHOD A)

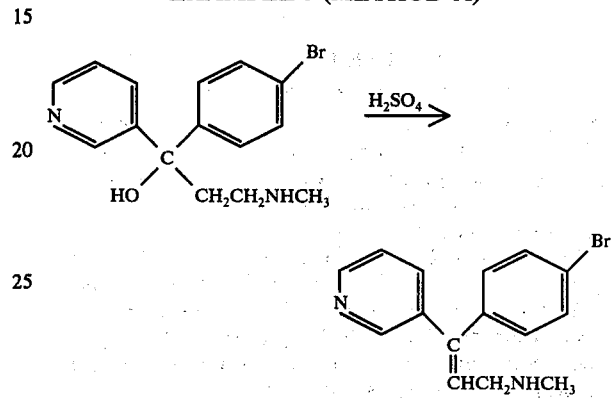

The raw product of 3-(4-bromophenyl)-3-hydroxy-N-methyl-3-(3-pyridyl)-propylamine (prepared in accordance with Example B from 5.0 g of 3-(4-bromophenyl)-3-hydroxy-N-methyl-3-pyridyl)propionamide) was added with stirring to 50% sulphuric acid (50 ml) and the mixture was heated at 110° for 10 minutes. The mixture was then cooled, poured on to crushed ice, made basic by the addition of 30% NaOH and extracted with ether. Evaporation gave 4.9 g of semicrystalline residue. 150 ml acetone was added and the solution was clarified by filtration. 0.9 g (0.1 mole) of oxalic acid dissolved in 25 ml of acetone was added dropwise to the filtrate. The white precipitate was collected and recrystallized from 350 ml isopropyl alcohol to yield 1.7 g of white crystals of the oxalate of 3-(4-bromophenyl)-N-methyl-3-(3-pyridyl)-allylamine. M.p. 180°-208° C. The NMR spectrum shows the vinyl proton as a double triplet at 6.1-6.4 ppm, indicating a mixture of E and Z isomers.

Isolation of the Z-isomer: After recrystallization three times from ethanol, 0.5 g substance was obtained. M.p. 202°-205° C. The NMR spectrum shows the vinyl proton as a single triplet with J = 3.4 Hz and in a position which indicates that the compound is the Z-isomer.

The amine oxalate obtained was converted into the corresponding hydrochloride via the free base. Recrystallization from acetonitrile containing a few percent of water gave a compound melting at 161°-165° C. Elemental analysis showed it to be a dihydrochloride with the composition $C_{15}H_{15}BrN_2 \cdot 2HCl \cdot H_2O$.

Isolation of the E-isomer: Mother liquors from the isolation of the Z isomer, containing both isomers in a ratio of about 60:40 E and Z respectively, was used. The oxalate of this amine mixture was recrystallized three times from acetonitrile containing 15% of water, giving a substance melting at 198°-201° C. According to the NMR spectrum this substance was the E isomer.

G) PHARMACOLOGICAL TESTS

It is not possible by experimental means to induce depressions in laboratory animals. In order to evaluate a possible anti-depressive effect of new substances biochemicalpharmacological test methods must be resorted to. One such method, which seems to give a good indication of the potential anti-depressive effects of the test substances, is described in Europ. J. Pharmacol. 17, 107, 1972.

This method involves the measurement of the decrease in the uptake of $^{14}C$-5-hydroxytryptamine ($^{14}C$-5-Ht) and $^3H$-noradrenaline ($^3H$-NA) in brain slices from mice after in vivo and in vitro administration of the test substance.

INHIBITION OF THE UPTAKE OF $^{14}C$-5-HT and $^3H$-NA IN VITRO AND IN VIVO

The test substances were administered intraperitoneally half an hour before the animals were killed. The midbrain was taken out, sliced and incubated in a mixture consisting of 0.2 nmole of $^{14}C$-5-HT, 0.2 nmole of $^3H$-NA and 11 μmole of glucose in 2 ml of Krebs-Henseleit buffer, pH 7.4 per 100 mg of brain slices. The incubation time was 5 minutes with 5 minutes of preincubation before the labelled amines were added. The slices were dissolved in Soluene ® and the amounts of radio-active amines taken up were determined by liquid scintillation. The doses producing 50 percent decrease of the active uptake ($ED_{50}$) of $^{14}C$-5-HT and $^3H$-NA were determined graphically from dose response curves. Active uptake is defined as that part of the radioactive uptake which is inhibited by a high concentration of cocaine.

In the in vitro method, slices of mouse midbrain were preincubated for 5 minutes with a solution of the compound to be tested and then incubated as described above.

As can be seen from the Table the compounds of the invention are potent inhibitors of the neuronal uptake of 5-hydroxytryptamine and noradrenaline. The Z-form of the compound of the invention shows a stronger inhibition of the uptake of 5-HT in vivo than do any of the prior art compounds tested.

The Z-form of the compound of the invention tested as the hydrochloride, is further a more potent inhibitor of the uptake of 5-HT in vitro than any of the prior art compounds. (The difference appearing between the oxalate and the hydrochloride is believed to be due to the fact that the hydrochloride was prepared from the oxalate whereby a more pure Z-isomer was obtained). The E-form of the compound of the invention primarily inhibits the uptake of noradrenaline. The inhibition of neuronal uptake of 5-hydroxytryptamine and noradrenaline disclosed, may give the compounds of the invention value as anti-depressive agents. Likewise the compounds of the invention may be useful as anxiolytic agents.

We claim:

1. A compound useful as an intermediate for the preparation of therapeutically valuable phenyl-pyridyl derivatives, which compound is characterized by the formula

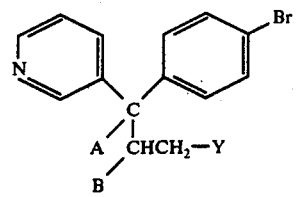

or an acid addition salt thereof, wherein Y is a member selected from the group consisting of a halogen, a methanesulfonyloxy group, a toluenesulfonlyloxy group and a benzenesulfonyloxy group and A and B together form a second bond or A is OH and B is H.

2. The compound of claim 1, wherein Y is a bromo group.

TABLE

Inhibition of neuronal uptake of 5-hydroxytryptamine and noradrenaline in slices from mouse brain

| | | Compound | | Uptake of $^{14}C$-5-HT | | Uptake of $^3H$-NA | |
|---|---|---|---|---|---|---|---|
| | | | | in vitro $EC_{50}$ μM | in vivo $ED_{50}$ μmole/kg i.pi | in vitro $EC_{50}$ μM | in vivo $ED_{50}$ μmole/kg |
| | R | somer | salt | | | | |
| Compounds of the invention | H | mixture | oxalate | 0.5 | 32 | —[1] | —[1] |
| | H | Z | oxalate | 0.5 | 18 | 2.5 | 102 |
| | H | Z | hydrochloride | 0.1 | 15.2 | 1.5 | >101[2] |
| | H | E | oxalate | 2.5 | 102 | 0.8 | 25 |
| Prior art compounds | $CH_3$ | Z | hydrochloride | 1.7 | 49 | 24.4 | >98 |
| | $CH_3$ | E | oxalate | 6.1 | >98 | 6.1 | 25 |
| | imipramine | | hydrochloride | 0.3 | 125 | 0.08 | 63 |

[1] not tested
[2] 39% inhibition recorded at the dose 101 μmole/kg i.p.

3. A compound having the formula

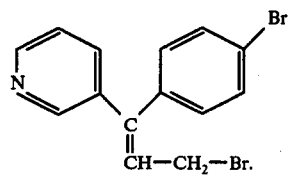
4. The compound of claim 1, wherein Y is a chloro group.
5. A compound having the formula
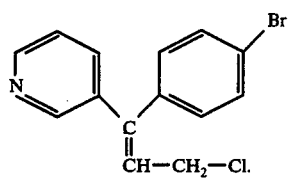
* * * * *